US00PP18530P3

(12) United States Plant Patent
Stemkens

(10) Patent No.: US PP18,530 P3
(45) Date of Patent: Feb. 26, 2008

(54) ***NEMESIA* PLANT NAMED 'NEMHAPIN'**

(50) Latin Name: ***Nemesia* hybrid**
Varietal Denomination: Nemhapin

(75) Inventor: Henricus G.W. Stemkens, Hoorn (NL)

(73) Assignee: Syngenta Seeds B.V., Enkhuizen (NL)

( * ) Notice: Subject to any disclaimer, the term of this patent is extended or adjusted under 35 U.S.C. 154(b) by 0 days.

(21) Appl. No.: 11/376,480

(22) Filed: Mar. 15, 2006

(65) Prior Publication Data

US 2007/0220645 P1 Sep. 20, 2007

(51) Int. Cl.
*A01H 5/00* (2006.01)

(52) U.S. Cl. ..... Plt./263

(58) Field of Classification Search ..... Plt./263
See application file for complete search history.

*Primary Examiner*—Wendy C. Haas
*Assistant Examiner*—Georgia Helmer
(74) *Attorney, Agent, or Firm*—Bruce Vrana

(57) ABSTRACT

A new and distinct variety of *Nemesia* plant, substantially as herein illustrated and described characterized particularly as to novelty by its semi-trailing and compact habit, pink flowers, a yellow palate, very early flowering and absolutely no need set.

1 Drawing Sheet

Latin name of the genus and species of the plant claimed: *Nemesia* hybrid.
Varietal denomination: 'Nemhapin'.

BACKGROUND OF THE NEW PLANT

The present invention relates to a new and distinct cultivar of *Nemesia* plant known botanically as *Nemesia* hybrid and that will be referred to hereinafter by the cultivar name 'Nemhapin.'

The new *Nemesia* is a product of a planned breeding program conducted in Enkhuizen, The Netherlands. The new *Nemesia* cultivar is characterized by a semi-trailing and compact habit, pink flowers, a yellow palate, very early flowering and absolutely no seed set.

The new *Nemesia* originated from a cross-pollination in 2002 of an unpatented *Nemesia* plant, named 'C0141-3,' as the female, or seed, parent with an unpatented *Nemesia* plant named 'C0099-2,' as the male, or pollen, parent. The cultivar 'Nemhapin' was discovered and selected as a plant within the progeny from this cross-pollination in a controlled environment in Enkhuizen, The Netherlands, in 2003.

As a result of this cross the present cultivar was created in 2003 in Enkhuizen, Netherlands and has been repeatedly asexually reproduced by cuttings in Enkhuizen, Netherlands and Sarrians, France over a two year period. It has been found to retain its distinctive characteristics through successive propagations. The new variety is stable and reproduces true to type in successive generations of asexual reproduction.

DESCRIPTION OF THE DRAWING

This new *Nemesia* plant is illustrated by the accompanying photographic drawing which shows blooms, buds and foliage of the plant in full color, the color shown being as true as can be reasonably obtained by conventional photographic procedures. The plant illustrated in the photographic drawing is a 15 week old plant.

DESCRIPTION OF THE NEW CULTIVAR

The following detailed descriptions set forth the distinctive characteristics of this new *Nemesia*. The data which defines these characteristics were collected from asexual reproductions carried out in Enkhuizen, Netherlands. The plant history was taken on 14 weeks old plants blossomed under natural light in a greenhouse and grown in a 10.5 cm container.

Color readings were taken in the greenhouse under ambient light. Color references are primarily to the R.H.S. Colour Chart of The Royal Horticultural Society of London.

TABLE 1

Differences between the new cultivar 'Nemhapin,' its parents and a similar cultivar

| | 'Nemhapin' | 'C0141-3' | 'C0099-2' | 'Lavender Sachet' |
|---|---|---|---|---|
| Seed set | No | Plentiful | Few | Plentiful |
| Flower size | Medium | Medium | Small | Medium |
| Flower color | Pink | Rose | White | Lavender pink |
| Palate color | Yellow | Yellow | White | White |

The commercial name of the most resembling variety is 'Lavender Sachet.' This variety is not known to be patented.

BOTANICAL DESCRIPTION OF THE PLANT

The plant:

*Classification.*—Botanical : *Nemesia*. Species : Hybrid.

*Parentage.*—Female parent : An inbred seedling named 'C0141-3' bred in 2001. Pollen parent : An inbred seedling named 'C0099-2' bred in 2001.

*Growth habit.*—Semi-trailing and compact.

*Plant height.*—14–24 cm.

*Spreading area of plant.*—22–30 cm.

*Branching chamber.*—Freely branching and lateral branching at every node.

*Number of branches per plant.*—30–60.
*Blooming period.*—From April until November.
*Propagation.*—Vegetative stem cuttings.
*Sexuality.*—Hermaphrodite.
*Time to initiate roots.*—Approximately 10 days at temperatures of 21 degrees centigrade is needed to produce rooted cuttings.
*Root system.*—Numerous and fine, the color is N155A.

The Stem:
*Diameter.*—3–4 mm.
*Length.*—10–12 cm.
*Shape.*—Quadrilateral with ridges.
*Anthocyanin pigmentation.*—Absent.
*Color of the stem.*—137C.
*Length of internode.*—20–30 mm.
*Pubescence.*—Glabrous.
*Length lateral branches.*—8–12 cm.

The foliage:
*Phyllotaxis.*—Opposite.
*Shape of blade.*—Broadly ovate.
*Attachment.*—Petiolate.
*Texture.*—Upper side : Glabrous. Lower side : Glabrous.
*Venation.*—Pinnate.
*Leaf margin.*—Serrate.
*Leaf base.*—Truncate.
*Leaf apex.*—Apiculate.
*Length.*—20–40 mm.
*Width.*—13–30 mm.
*Depth of incision.*—1–2 mm.
*Color.*—Upper side : 137B. Lower side : 138C.
*Petiole length.*—1–2 mm.
*Petiole surface structure.*—Glabrous.
*Petiole diameter.*—2–3 mm.
*Petiole coloration.*—Upper side : 137B. Lower side : 138C.

The Bud:
*Peduncle length.*—10–25 mm, depending on season.
*Peduncle diameter.*—2–3 mm.
*Peduncle color.*—137B.
*Peduncle surface.*—Glabrous.
*Pedicel length.*—4–10 mm.
*Pedicel diameter.*—Less than 1 mm.
*Pedicel color.*—137C.
*Pedicel surface.*—Glabrous.
*Stipule length.*—1–2 mm.
*Stipule width.*—1–2 mm.
*Stipule shape.*—Lanceolate.
*Stipule color.*—Upper side : 137C. Lower side : 137C.
*Bud size.*—Diameter : 4 mm. Length : 3–5 mm.
*Bud shape.*—Globular.
*Bud color.*—N155B.
*Bud surface.*—Glabrous.
*Sepals.*—Color (Upper side) : 137B. Color (Lower side) : 137B. Form : Upright. Surface : Glabrous. Number : 5, fused. Length : 1–2 mm. Width : Less than 1 mm. Shape : Lanceolate. Apex : Apiculate. Base : Fused. Margin : Entire.

The Flower:
*Type of inflorescence.*—Axillary raceme.
*Flower shape.*—Personate.
*Palate color.*—2B in the center and 2D to the right and left sides of the center.
*Nectary* (*located on underside of palate*).—4 mm in width and 4 mm in length.
*Nectary color.*—159D.
*Throat color* (*Upper surface*).—158D.
*Throat color* (*Lower surface*).—157C.
*Surface of upper lip.*—Upper side : Glabrous. Lower side: Glabrous.
*Surface of lower lip.*—Upper side : Glabrous. Lower side : Glabrous.
*Lip margin* (*lower lip*).—Entire.
*Lip margin* (*upper lip*).—Entire.
*Number of lips.*—2.
*Lobes.*—Upper lip : 4. Lower lip : 1.
*Lobes on upper lip fused or unfused.*—Fused.
*Lip apex* (*Upper lip*).—Each lobe has a rounded apex.
*Lip base* (*Upper lip*).—Fused.
*Lip apex* (*Lower lip*).—Obtuse.
*Lip base* (*Lower lip*).—Fused.
*Upper lip color.*—Upper side : 70C. Lower side : 70D.
*Lower lip color.*—Upper side : 70C. Lower side : 70D.
*Flower dimensions.*—1.2 cm in depth, 1.8 cm in length and 2 cm in width at widest part.
*Lower lip dimensions.*—1.1 cm in length and 1.4 cm in width.
*Upper lip dimensions.*—0.9 cm. in length and 2.1 cm in width.
*Lobe dimensions* (*Upper lip*).—1 cm in length and 5 mm in width.
*Flower spur dimensions.*—1 cm in length and 1–2 mm in diameter.
*Spur color.*—N155D.
*Calyx dimensions.*—4 mm in length and 5 mm in width.
*Calyx color.*—135A.
*No. of flowers per inflorescence.*—40–50.
*Fragrance.*—A very light perfume fragrance occurs.
*Bloom time of one inflorescence.*—New florets continue to open in one inflorescence over a period of 32 days.
*Lastingness of one flower.*—3–7 days.

The Reproductive Organs:
*Androecium.*—Stamens quantity : 4. Anther shape : Ovoid. Anther length : 0.3 mm. Anther width : 0.2 mm. Anther color : 154C. Pollen amount : Scarce pollen. Pollen color : 154D.
*Gynoecium.*—Pistils quantity : 1. Pistil length : 3–5 mm. Stigma color : 144C. Style length : 3–5 mm. Style color : 144D. Ovary color : 144C. Ovary position : Superior. Ovary shape : Oval. Ovary dimensions : 0.3 mm in width and 0.4 mm in length.

Seeds: No seed set is observed. No fruits are developed.

Disease and Pest Resistance: There are no disease problems known to the inventor other than what affects typical *Nemesia*.

Strength: Resistant to temperatures ranging from 0 to 32 degrees Celsius.

What is claimed is:

1. A new and distinct cultivar of *Nemesia* plant named 'Nemhapin,' as substantially illustrated and described herein.

* * * * *

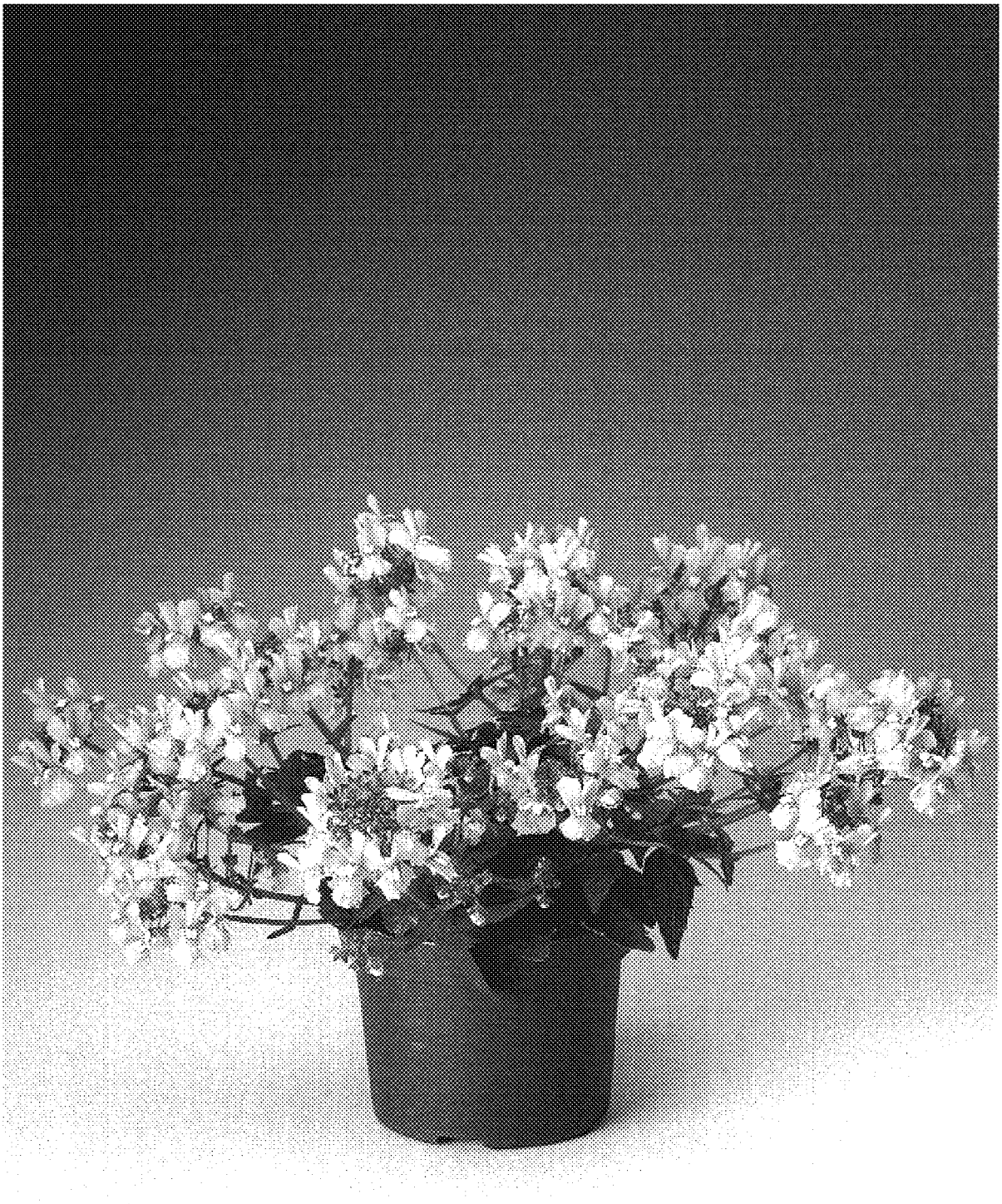

UNITED STATES PATENT AND TRADEMARK OFFICE

CERTIFICATE OF CORRECTION

PATENT NO. : PP 18,530 P3
APPLICATION NO. : 11/376480
DATED : February 26, 2008
INVENTOR(S) : Stemkens It is certified that error appears in the above-identified patent and that said Letters Patent is hereby corrected as shown below:

Title page, item [57] in the ABSTRACT, insert --,-- following "described" and delete "need" and insert therefor --seed--

Signed and Sealed this

Twenty-seventh Day of May, 2008

JON W. DUDAS
*Director of the United States Patent and Trademark Office*